United States Patent
Sumanaweera et al.

(10) Patent No.: US 8,315,691 B2
(45) Date of Patent: Nov. 20, 2012

(54) RADIOSURGICAL ABLATION OF THE MYOCARDIUM

(75) Inventors: Thilaka Sumanaweera, Los Altos, CA (US); Patrick Maguire, Menlo Park, CA (US); Roderick A. Young, Stanford, CA (US)

(73) Assignee: CyberHeart, Inc., Menlo Park, CA (US)

( * ) Notice: Subject to any disclaimer, the term of this patent is extended or adjusted under 35 U.S.C. 154(b) by 826 days.

(21) Appl. No.: 12/238,809

(22) Filed: Sep. 26, 2008

(65) Prior Publication Data

US 2009/0080610 A1    Mar. 26, 2009

Related U.S. Application Data

(60) Provisional application No. 60/975,373, filed on Sep. 26, 2007.

(51) Int. Cl.
*A61B 6/00* (2006.01)
(52) U.S. Cl. ........ 600/436; 600/407; 600/424; 600/417; 600/429; 606/47; 606/50
(58) Field of Classification Search .................. 600/407, 600/424, 429, 417, 436; 606/32–35, 47, 606/50
See application file for complete search history.

(56) References Cited

U.S. PATENT DOCUMENTS

| | | | |
|---|---|---|---|
| 5,590,657 A | 1/1997 | Cain et al. | |
| 5,764,723 A | 6/1998 | Weinberger et al. | |
| 6,093,141 A | 7/2000 | Mosseri et al. | |
| 6,198,959 B1 * | 3/2001 | Wang | 600/413 |
| 6,351,662 B1 | 2/2002 | Franck et al. | |
| 6,402,762 B2 | 6/2002 | Hunter et al. | |
| 6,558,382 B2 | 5/2003 | Jahns et al. | |
| 6,658,285 B2 | 12/2003 | Potse et al. | |
| 6,760,620 B2 | 7/2004 | Sippens Groenewegen | |
| 6,889,695 B2 * | 5/2005 | Pankratov et al. | 128/898 |
| 2003/0153802 A1 | 8/2003 | Bonan et al. | |
| 2005/0161051 A1 | 7/2005 | Pankratov et al. | |
| 2006/0178719 A1 | 8/2006 | Ideker et al. | |
| 2007/0167801 A1 * | 7/2007 | Webler et al. | 600/459 |

FOREIGN PATENT DOCUMENTS

WO    WO2005/000102 A2    1/2005

OTHER PUBLICATIONS

International Preliminary Report on Patentability of PCT Application No. PCT/US2008/077816, mailed Apr. 8, 2010, 6 pages total.

(Continued)

*Primary Examiner* — Brian Casler
*Assistant Examiner* — Joel Lamprecht
(74) *Attorney, Agent, or Firm* — Kilpatrick Townsend and Stockton LLP (57) ABSTRACT

The invention provides a non-invasive system and method for treatment of the heart. In a first aspect, a method for treatment of an anatomical site related to arrhythmogenesis of a heart of a patient comprises creating a target shape encompassing the anatomical site, directing particle beam radiation or x-ray radiation from outside the patient toward the target shape wherein one or more doses of radiation ablates the target shape and disregarding at least one orientation of cardiac motion while creating the target shape or directing the particle beam or both.

32 Claims, 6 Drawing Sheets

OTHER PUBLICATIONS

Accuray Incorporated, "The Complete Solution", Accuray Incorporated, no date, 3 pages total.

Chinitz, Jason S., et al. "Atrial fibrillation is common after ablation of isolated atrial flutter during long-term follow-up", *Heart Rhythm* (2007) 4(8):1029-1033.

Argenziano, M.D., "Surgical Pulmonary Vein Isolation in Patients with Atrial Fibrillation," Columbia-Presbyterian Medical Center, no date, 6 pages total.

Damiano, Jr., M.D. "An Overview of Current Alternative Energy Sources for the Surgical Treatment of Atrial Fibrillation," Washington University School of Medicine, no date, 2 pages total.

Dictionary.com, definition of the word "dynamic," downloaded from <<http://dictionary.reference.com/search?q=dynamic>>, on Sep. 14, 2004, 3 pages total.

Dictionary.com, definition of the word "register," downloaded from <<http://dictionary.reference. com/search?q=register&r=67>>, on Sep. 13, 2004, 8 pages total.

Gerszen, M.D., "CyberKnife offers frameless stereotactic radiosurgery, marking revolutionary new way to treat spine lesions," *Neurosurgery News* Summer 2001, 2:3, 1 page total.

Kluiwstra, et al. "Ultrasound Phased Arrays for Noninvasive Myocardial Ablation: Initial Studies," 1995 IEEE Ultrasonic Symposium, pp. 1605-1608.

Kress, M.D., "Surgical Ablation of Atrial Fibrillation: Is There a "Best" Lesion Pattern?," Heart Surgery Forum Reviews, no date, 1:1, pp. 11-12.

Levin, "Accuray: Tightly Targeting Tumors," In Vivo, Apr. 2001, 19:4, pp. 1-12.

Martinez, Cyberknife Offers Targeted, Painless and Fast Treatment, Georgetown Physician Update, Mar./Apr. 2002, 1:2, 2 pages 2 total.

Regar, et al., "Coronary Brachytherapy," no date, 8 pages total.

The Gray Sheet, "CyberKnife Slices Radiosurgery Field, Possible for Non-Malignant Conditions," The Gray Sheet, Dec. 2003, 29:48, 2 pages total.

\* cited by examiner

RADIOSURGICAL ABLATION OF THE MYOCARDIUM

CROSS-REFERENCES TO RELATED APPLICATIONS

This application claims the benefit under 35 USC 119(e) of U.S. Provisional Application No. 60/975,373, filed Sep. 26, 2007, entitled "Radiosurgical Ablation of the Myocardium", the full disclosure of which is incorporated herein by reference. This application is related to U.S. Pat. No. 6,889,695 entitled "Method for Non-Invasive Heart Treatment", the contents of which are incorporated herein by reference.

BACKGROUND OF THE INVENTION

The present invention is generally related to treatment of the heart, and in particular, non-invasive treatment of the heart using radiosurgical ablation.

A typical adult human heart beats at a rate of about 70 beats per minute. The rate is not constant, however, and changes during and following exercise, with fear or anxiety, or for other reasons. A heart can also pump arrhythmically for many reasons, including damage to the heart's electrical conduction system. Arrhythmias interfere with the heart's ability to pump blood, and can result in severe symptoms, including death.

Atrial fibrillation is one of the most common cardiac arrhythmias. Atrial fibrillation occurs in as many 50% of patients undergoing cardiac operations. Patients with chronic atrial fibrillation may suffer from symptomatic tachycardia or low cardiac output, have a risk of thromboembolic complications, and are at risk for death. Until just a few years ago many health care providers thought atrial fibrillation to be a "nuisance" arrhythmia with few consequences. However, medical research has uncovered some devastating complications, including stroke, congestive heart failure, and cardiomyopathy. Many conditions have been associated with atrial fibrillation, including thyroid disorders, valve disease, hypertension, sick sinus syndrome, pericarditis, lung disease, and congenital heart defects. Atrial fibrillation can occur at any age, but its prevalence tends to increase with age and effects men slightly more often than women.

During atrial fibrillation, the atria lose their organized pumping action. In normal sinus rhythm, the atria contract, the valves open, and blood fills the ventricles (the lower chambers). The ventricles then contract to complete the organized cycle of each heart beat. Atrial fibrillation has been characterized as a storm of electrical energy that travels across the atria, causing these upper chambers of the heart to quiver or fibrillate. During atrial fibrillation, the blood is not able to empty efficiently from the atria into the ventricles with each heart beat. Blood can then pool and become stagnant in the atria, creating a site for blood clot formation. Such clot formation can become a primary source of stroke in patients with atrial fibrillation.

Non-surgical treatments are sometimes effective in treating atrial fibrillation. Several drugs are known, but may have significant side effects and are not ideal for treatment of acute fibrillation. Pharmacological therapies are also associated with adverse effects in a significant proportion of patients. Moreover, although electrical cardioversion (alone or in combination with anti-arrhythmic therapy) is often effective in restoring sinus rhythm, high recurrence rates of atrial fibrillation have been reported.

A number of invasive surgical procedures have been proposed for treatment of atrial fibrillation. Invasive procedures involving direct visualization of the tissues include the Maze procedure. Dr. James Cox and others proposed the original Cox-Maze procedure in which the atria are surgically dissected and then repaired. In the Maze procedure, for example, ectopic re-entry pathways of the atria are interrupted by the scar tissue formed using a scalpel or the like. The pattern of scar tissue prevented recirculating electrical signals which can result in atrial fibrillation.

The Maze surgical procedure has been simplified by the use of cryoprobes, radio frequency (RF) probes, and laser probes to effect the pattern of scar tissue. For example, ablation is sometimes used to terminate arrhythmias by introducing a catheter into the heart and directing energy at specific areas of heart tissue. By using a transarterial catheter to deliver the energy to the atria under fluoroscopy, interventional cardiologists have treated atrial fibrillation in a less-invasive manner. RF energy has been used successfully to terminate arrhythmias by introducing the catheter into the heart and directing the RF energy at specific areas of the heart tissue. Nonetheless, there is still a need for improved non-invasive treatments of arrhythmia.

BRIEF SUMMARY OF THE INVENTION

The present invention provides non-invasive methods for treatment of the heart.

In a first aspect, the invention provides a method for treatment of an anatomical site related to arrhythmogenesis of a heart of a patient. The method comprises creating a target shape encompassing the anatomical site, directing particle beam radiation or x-ray radiation from outside the patient toward the target shape wherein one or more doses of radiation ablates the target shape and disregarding at least one orientation of cardiac motion.

In some embodiments, the target shape encompasses both rhythms of ventricular tachycardia and ventricular fibrillation and the anatomical site includes a valve annulus, a ventricular site, ventricular outflow tract, or within or outside of a ventricular aneurysm.

In some embodiments, creating the target shape includes registration by combining two or more images selected from the group consisting of a Computer Tomography (CT) scan, a Magnetic Resonance Image (MRI) scan, a sonogram, an X-ray, an angiogram and an electrophysiologic map. In some embodiments, creating the target shape includes using one or more fiducials.

In another aspect, the invention provides a system for treatment of an anatomical site related to arrhythmogenesis of a heart of a patient. The system comprises an apparatus configured to create a target shape encompassing the anatomical site, wherein the apparatus disregards at least one orientation of cardiac motion, including not compensating for cardiac motion of less than 2 mm, and a particle beam radiation or x-ray radiation device configured to direct one or more doses of radiation from outside the patient toward the target shape to ablate the target shape.

DETAILED DESCRIPTION OF THE INVENTION

Radiosurgery is a known method of treating tumors in the body. The radiation can be delivered invasively in conjunction with traditional scalpel surgery, or through a percutaneous catheter. Radiation can also be delivered non-invasively from outside the body, through overlying tissue. Advances in stereotactic surgery have provided increased accuracy in registering the position of tissue targeted for treatment and a radiation source. For example, see U.S. Pat. Nos. 6,351,662 and 6,402,762. Stereotactic radiosurgery systems may be commercially available from ACCURAY, INC. of Sunnyvale, Calif., and BRAINLAB. The Accuray Cyberknife™ stereotactic radiosurgery system has reportedly been used to provide targeted, painless, and fast treatment of tumors.

Figure 1:
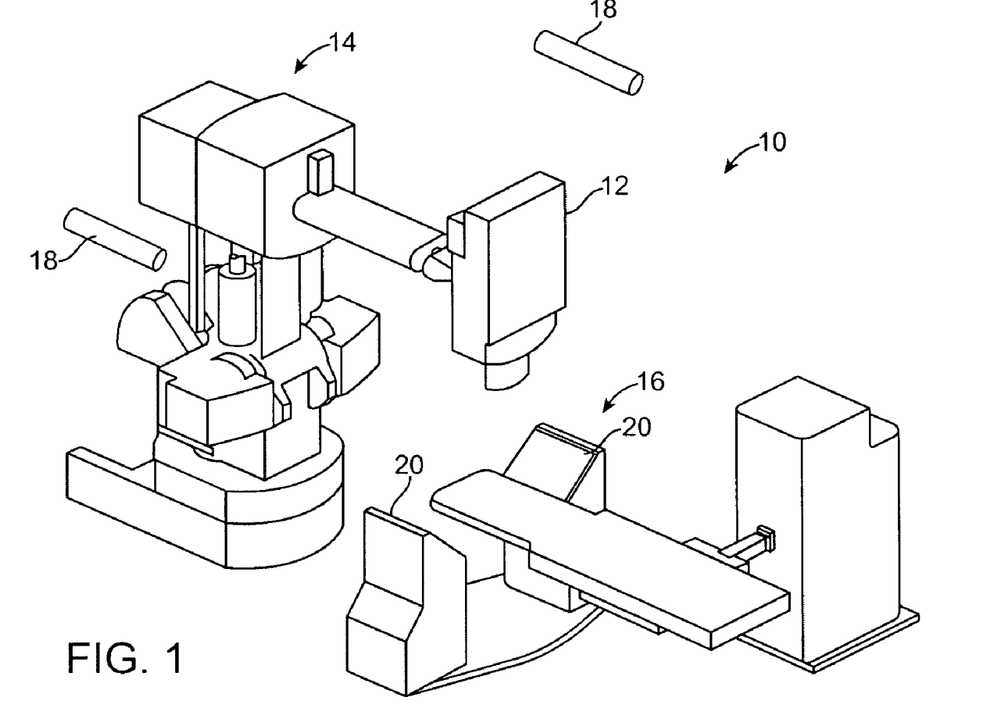
FIG. 1 is a perspective view of a radiation treatment system.

An exemplary Cyberknife stereotactic radiosurgery system 10 is illustrated in FIG. 1. Radiosurgery system 10 has a single source of radiation, which moves about relative to a patient. Radiosurgery system 10 includes a lightweight linear accelerator 12 mounted to a highly maneuverable robotic arm 14. An image guidance system 16 uses image registration techniques to determine the treatment site coordinates with respect to linear accelerator 12, and transmits the target coordinates to robot arm 14 which then directs a radiation beam to the treatment site. When the target moves, system 10 detects the change and corrects the beam pointing in near real-time. Near real-time image guidance may avoid any need for skeletal fixation to rigidly immobilize the target.

Improvements in imaging and computer technology have led to advances in radiation treatment, often for targeting tumors of the spine and brain. The introduction of CT scanners enables surgeons and radiation oncologist to better define the location and shape of a tumor. Further improvements in imaging technology include MRI and PET scanners. In addition, radiation therapy has also been aided by enhancements in ancillary technologies such as simulators to help position patients and advanced computers to improve treatment planning to enable the radiation oncologist to deliver radiation from a number of different angles. Computer technology has been introduced that enable radiation oncologists to link CT scanners to radiation therapy, making treatment more precise and treatment planning faster and more accurate, thereby making more complex plans available. Such advancements allow integrated conformal therapy, in which the radiation beam conforms to an actual shape of a tumor to minimize collateral damage to the surrounding healthy tissue. By combining simulators and imaging and treatment planning computers, the irradiation can be precisely administered.

System 10 makes use of robot arm 14 and linear accelerator 12 under computer control. Image guidance system 16 can monitor patient movement and automatically adjust system 10 to maintain radiation registration with the selected target tissue. Rather than make use of radiosurgery system 10 and related externally applied radiosurgical techniques to tumors of the spine and brain tissues, the invention applies system 10 to numerous cardiac conditions, and in one exemplary method to the treatment of atrial fibrillation (AF).

Tradition radiosurgery instruments without image guidance technology rely on stereotactic metal frames screwed into the patient's skull to accurately target a tumor. Traditional radiosurgery has its drawbacks, the biggest of which relate to the use of the frame, including the pain and difficulty of accurately reattaching the frame in precisely the same location, along with the inability to target tissues other than those in the neck and head. Conventional linear accelerators for these systems can also be the size and weight of an automobile. Frame-based radiosurgery is generally limited to isocentric or spherical target treatments. To allow a device which can precisely pinpoint and treat tissues throughout the body, system 10 makes use of a portable linear accelerator, such as those originally designed for industrial inspections, which can be carried on a person's back. Linear accelerators may be commercially available from SCHONBERG RESEARCH GROUP, SIEMENS, PICKER INTERNATIONAL INC. or VARIAN.

System 10 allows intensity modulated radiation therapy. Using computerized planning and delivery, intensity modulated radiation therapy conforms the radiation to the shape of (for example) a tumor. By using computers to analyze the treatment planning options, multiple beams of radiation match the shape of the tumor. To allow radiosurgery, system 10 can apply intense doses of high-energy radiation to destroy tissue in a single treatment. Radiosurgery with system 10 uses precise spatial localization and large numbers of cross-fired radiation beams. Because of the high dosage of radiation being administered, such radiosurgery is generally more precise than other radiation treatments, with targeting accuracies of 1 to 2 mm.

Linear accelerator 12 is robotically controlled and delivers pin-point radiation to target regions throughout the body of the patient. Radiation may be administered by using a portable linear accelerator such as that illustrated in FIG. 1. Larger linear accelerators may also generate the radiation in some embodiments. Such linear accelerators may be mounted on a large rotating arm that travels around the patient, delivering radiation in constant arcs. This process delivers radiation to the target tissue and also irradiates a certain amount of surrounding tissue. As a result, such radiation therapy may be administered in a series of relatively small doses given daily over a period of several weeks, a process referred to as fractionation. Each radiation dose can create some collateral damage to the healthy surrounding tissue.

In the exemplary embodiment, robot arm 14 of system 10 is part of a pure robotics system, providing six degree of freedom range of motion. In use, the surgeon basically pushes a button and the non-invasive procedure is performed automatically with the image guidance system continuously checking and re-checking the position of the target tissue and the precision with which linear accelerator 12 is firing radiation at the tumor. Image guidance system 16 provides x-ray image guidance that gives the surgeon the position of internal organs and skeletal anatomy. Image guidance system 16 continuously checks, during a procedure, that the target is at the same place at the end of the treatment that it was at the beginning. The exemplary image guidance system included with the Accuray CyberKnife™ radiosurgery system takes the surgeon's hand out of the loop. The surgeon may not even be in the operating room with the patient. Instead, the image guidance system guides the procedure automatically on a real-time basis. By combining advanced image guidance and robotics, system 10 has proven effective in treating head and neck tumors without having to resort to stereotactic metalframe screwed into the skull of a patient.

Image guidance system 16 includes diagnostic x-ray sources 18 and image detectors 20, this imaging hardware comprising two fixed diagnostics fluoroscopes. These fluoroscopes provide a stationary frame of reference for locating the patient's anatomy, which, in turn, has a known relationship to the reference frame of robot arm 14 and linear accelerator 12. System 10 can determine the location of the skull or spine in the frame of reference of the radiation delivery system by comparing digitally reconstructed radiographs derived from the treatment planning images with radiographs acquired by the real-time imaging systems of the fluoroscopes.

Once the skeletal position is determined, the coordinates are relayed to robot arm 14, which adjusts the pointing of linear accelerator 12 and radiation is delivered. The speed of the imaging process allows the system to detect and adjust to changes in target position in less than one second. The linear accelerator is then moved to a new position and the process is repeated. Alternative systems may make use of laser triangulation, which refers to a method of using so-called laser tattoos to mark external points on the skin's surface so as to target the location of internal organs and critical structures. An alternative system commercialized by BRAINLAB uses a slightly different approach that measures chest wall movements.

The exemplary CyberKnife™ radiosurgery system is currently available for treatment of lesions throughout the cervical spine. These lesions may be benign or malignant, such as metastasis, meningiomas, and arterial venous malformations, the CyberKnife™ radiosurgery system has been used to successfully treat metastic lesions in patients who are otherwise not candidates for surgery or lesions which are not amenable to open techniques. Progress has also been reported in developing the CyberKnife™ radiosurgery system for use in the thoracic and lumbar regions as well, with preliminary experience being indicated as promising. System 10 combines robotics and advanced image-guidance to deliver true frameless radiosurgery. Multiple beams of image guided radiation are delivered by robot arm 14 mounted linear accelerator 12. The radiation can converge upon a tumor, destroying it while minimizing exposure to surrounding healthy tissue. Elimination of a stereotactic frame through the use of image guided robotics enables system 10 to treat targets located throughout the body, not just in the head. Radiosurgery is thus possible in areas such as the spine that have traditionally been difficult to treat in the past with radiosurgery, and for pediatric patients such as infants, whose skulls are too thin and fragile to undergo frame-based treatment.

System 10 allows ablation of tissue anywhere in the patient's body. The present invention uses high energy x-ray irradiation from a linear accelerator mounted on a robot arm to produce ablation of cardiac tissue. In one example, system 10 is used to create lesions on the heart, such as for a Maze procedure. In another example, system 10 is used to ablate tumors or other defects of the heart treatable with radiation.

For heart treatments, the image-guidance tracks small markers or fiducials to target radiation. Advantages of system 10 include a treatment which can be provided on an outpatient basis, providing a painless option without the risk of complications associated with open surgery. Treatment may be applied in a single-fraction or hypo-fractionated radiosurgery (usually 2 to 5 fractions) for treatment near sensitive structures. System 10 provides flexibility in approach through computer control of flexible robotic arm 14 for access to hard-to-reach locations. System 10 allows isocentric (for spherical) or non-isocentric (for irregularly shaped) target shapes. The creation of the target shapes also takes into account critical surrounding structures, and through the use of robotic arm 14, harm to the critical structures surrounding may be reduced. After careful planning, the precise robotic arm can stretch to hard-to-reach areas. The precise radiation delivered from the arm then minimizes the chance of injury to critical surrounding structures, with near-real-time image-guidance system 16 eliminating the need for rigid immobilization, allowing robot arm 12 to track the body throughout the treatment.

Figure 2:
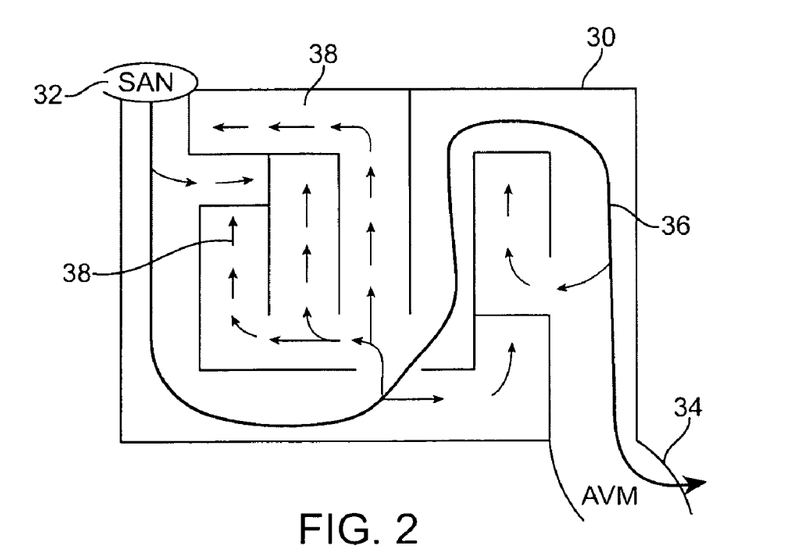
FIG. 2 is a schematic illustration of a simplified Maze lesion pattern.

Referring now to FIG. 2, Cox and his colleagues first described the Maze procedure for treatment of atrial fibrillation. In the original Maze procedure, ectopic re-entry pathways of the atria are interrupted by introducing scar tissue using a scalpel. In FIG. 2, a simple Maze path is conceptually illustrated. Maze lesion pattern 30 has one entrance 32, one exit 34, and one through path 36 with multiple blind alleys 38. Since the initial description of the Maze procedure by Cox and colleagues, a number of related open surgical approaches have been devised for the treatment of atrial fibrillation. Although successful in the irradication of atrial fibrillation in a high percentage of cases, these procedures are invasive, requiring median sternotomy, cardiopulmonary bypass, cardioplegic arrest, extensive cardiac dissection, and/or multiple atrial incisions. These procedures are also associated with significant morbidity. There are a number of iterations of the Cox procedure, including the Cox-Maze III procedure. While this operation has proven to be effective, it has significant shortcomings. The performance of the Cox-Maze III procedure requires cardiopulmonary bypass and an arrested heart. In most hands, it adds significantly to the cross-clamp time. Because of its perceived difficulty, few surgeons have learned to perform this operation. Finally, there is significant morbidity, particularly in terms of pacemaker requirements. These problems have led researchers to evaluate strategies to simplify the surgical treatment of atrial fibrillation.

Figure 3A:
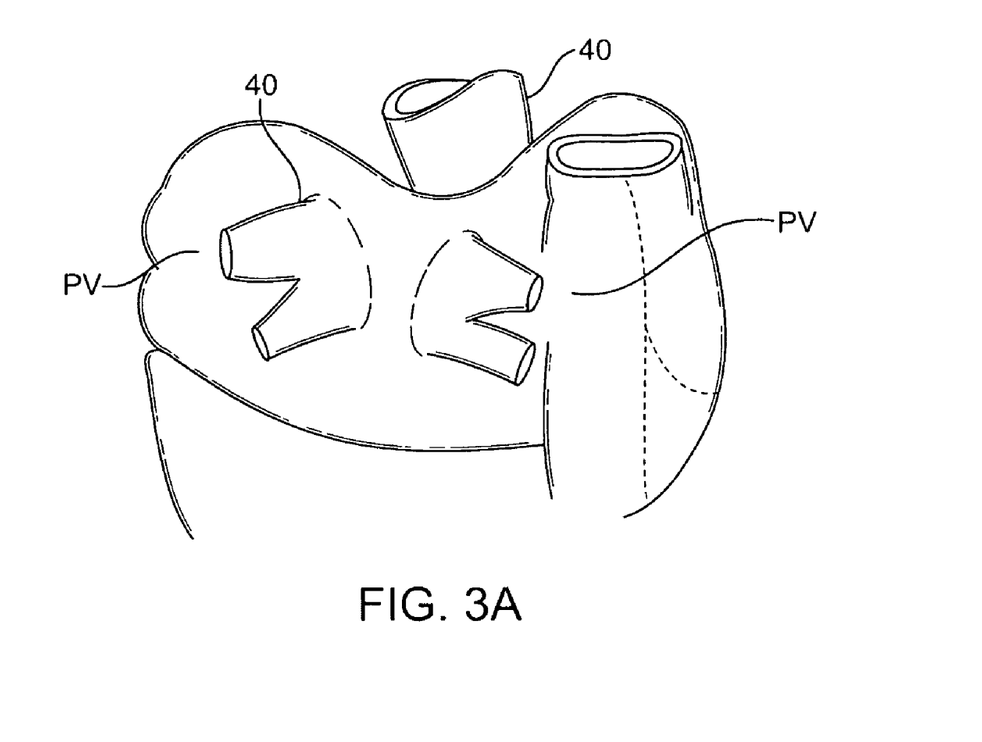
FIGS. 3A-3D illustrate alternative patterns of lesions in the heart for treatment of arrhythmia.

It has been suggested that in many patients, atrial fibrillation may be caused by re-entry wavelets limited to specific areas near the origins of the pulmonary veins. Success has also been reported with more limited procedures aimed at electrical isolation with discreet atrial lesions, utilizing atriotomy, radiofrequency ablation, or cryoablation. As can be understood with reference to FIGS. 3A through 3D, alternative approaches have involved both investigating different lesion sets and using a variety of energy sources to create linear lesions of ablation to replace the more time-consuming surgical incisions FIG. 3A illustrates lesions 40 effecting isolation of the pulmonary veins PV. These lesions abolish paroxysmal atrial fibrillation. The patterns mentioned above, except the Star procedure and the Leipzig lesion pattern isolate the pulmonary veins. Intraoperative measurements of pulmonary vein electrograms pre- and post-ablation to insure electrical silence of the muscle sleeves where triggers are thought to reside may confirm transmurality during application. Data suggests that in fifty percent of patients, effective therapy may be achieved by simply encircling the pulmonary veins with non-conductive lesions.

Lesion patterns may be tailored for the patient. For example, it has been shown that repetitive electrical activity originates in the left atrial appendage in patients with mitral valve disease. Electrical isolation of the left atrial appendage should be strongly considered in these patients. The tri-ring lesion pattern isolates the left atrial appendage, the pulmonary veins, and makes two connecting lesions. Atrial fibrillation associated with right atrial enlargement in congenital heart disease, or atrial flutter following right atrial incisions in congenital heart procedures do not imply the need for such lesions in the majority of patients undergoing atrial fibrillation ablation. The right atrium has a longer effective refractory period than the left atrium and in general sustains only longer re-entry circuits, the most common being the counterclockwise circuit of typical atrial flutter. This can be ablated by a transmural lesions connecting the tricuspid annulus to the IVC. Additional lesions connecting a lateral right atriotomy to the IVC or coronary sinus to the IVC may ablate an atypical right atrial flutter. In general, epicardial ablation may be safer than endocardial ablation because the energy source is directed into the atrial chamber rather than outward into adjacent mediastinal structures.

If bilateral pulmonary vein isolation is the irreducible component of surgical ablation, here is a possible schema for adding additional lesions for a particular patient:

1. If associated with mitral valve disease, include left atrial appendage isolation and left atrial appendage connecting lesion.

2. If known left atrial flutter (rare) include MV, TV, and LA appendage connecting lesions.

3. If known right atrial flutter, giant right atrium, or planned right atriotomy, include ablation lesions from TV to IVC; consider additional lesions from CS to IVC and from atriotomy to IVC.

4. If giant left atrium, consider LA reduction at time of procedure.

The legion pattern may be based on considerations of safety. There is no lesion pattern that is "best" for all patients, but the least complicated lesion pattern that is safe and easy to deliver and shown to be effective for a given population can be considered the best for those patients.

Figure 3B:
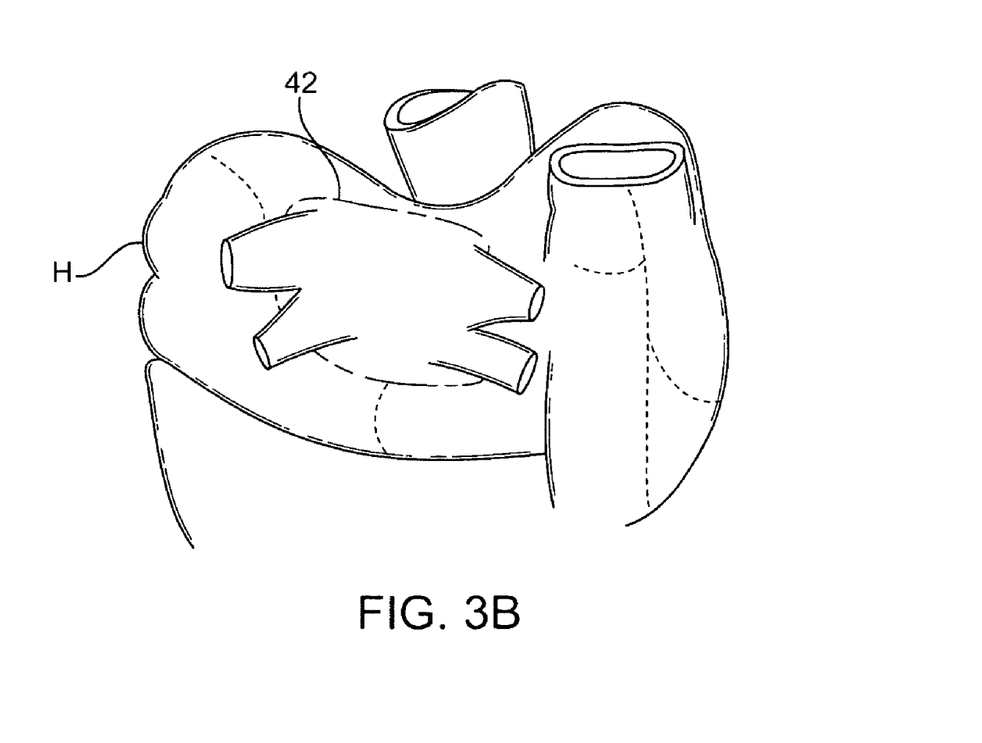
Figure 3C:
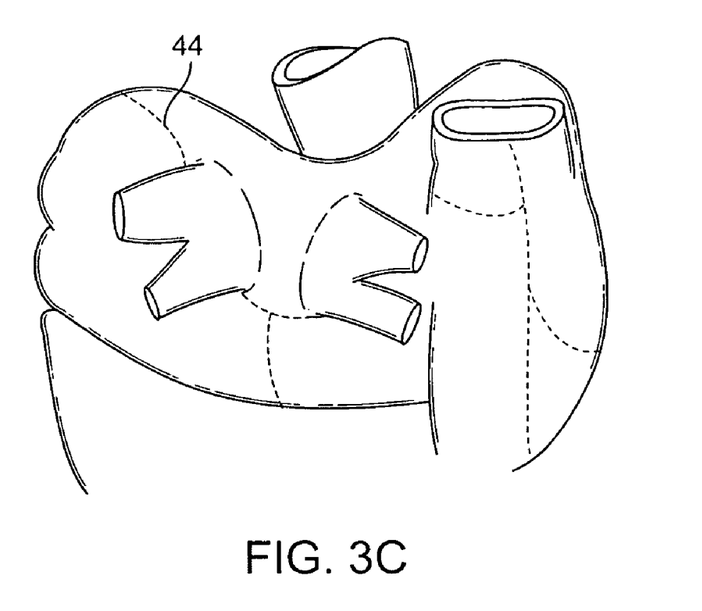
Figure 3D:
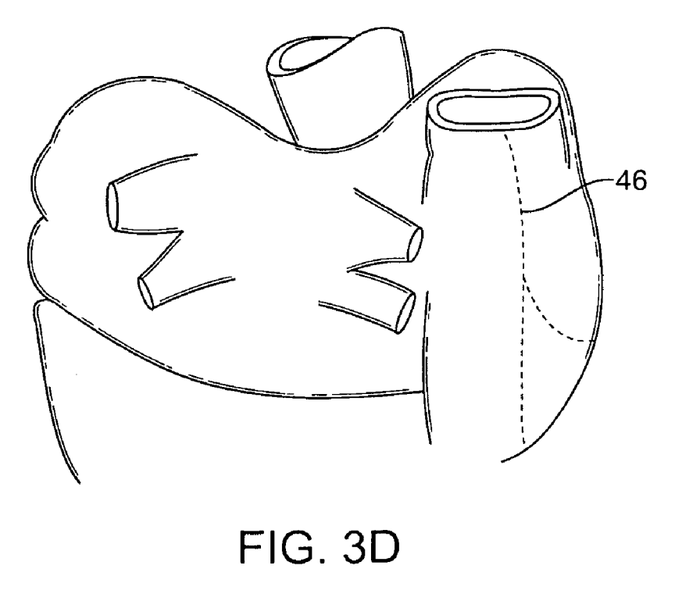

Referring now to FIG. 3B, a standard Maze III procedure has a lesion pattern 42 in heart H as illustrated. A modified Maze III procedure is illustrated in FIG. 3C, having a lesion pattern 44 applied in cryosurgical procedures. In FIG. 3D, a right atrial lesion 46 abolishes atrial flutter that occurs in the right atrium. However, most atrial flutter in the right atrium can be abolished by a single lesion in the isthmus below the OS of the coronary sinus.

Instead of cutting tissue using a Cox-Maze III, or other surgical procedure, and rather than invasive destruction of tissue using a cryoprobes or the like, radiosurgery system 10 (see FIG. 1) provides the ability to target specific foci, regions, lines, and so forth non-invasively. In a preferred embodiment, one could begin with the pulmonary veins, and then iteratively add additional lesions until atrial fibrillation is controlled. The exact doses of radiation will likely differ from patient to patient. A preferred basis for determining dosage is currently known treatment parameters used to produce lesions of similar tissues.

Figure 4A:
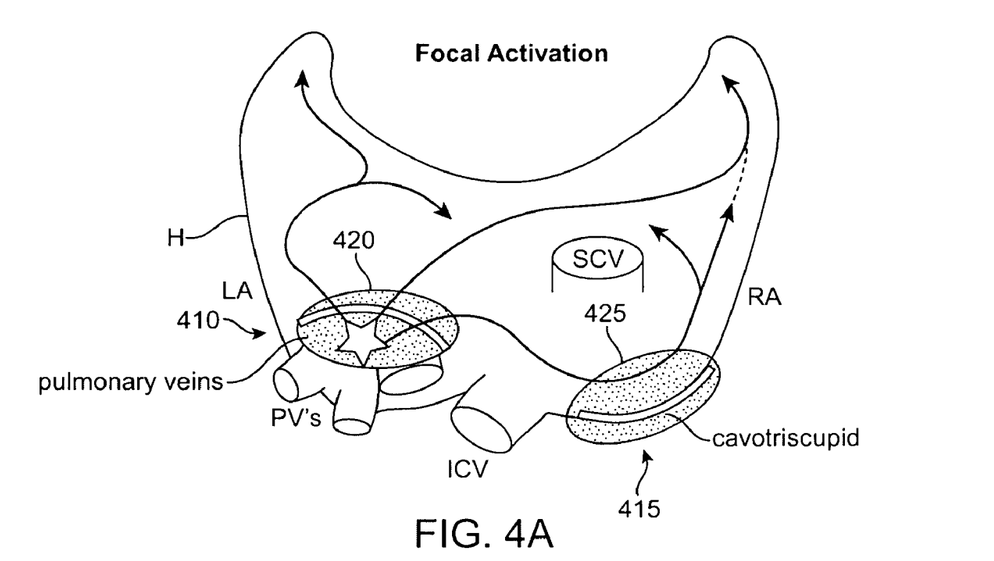
FIG. 4A-4B illustrate target shapes for radiosurgical ablation of the myocardium at one or more anatomical sites.
Figure 4B:
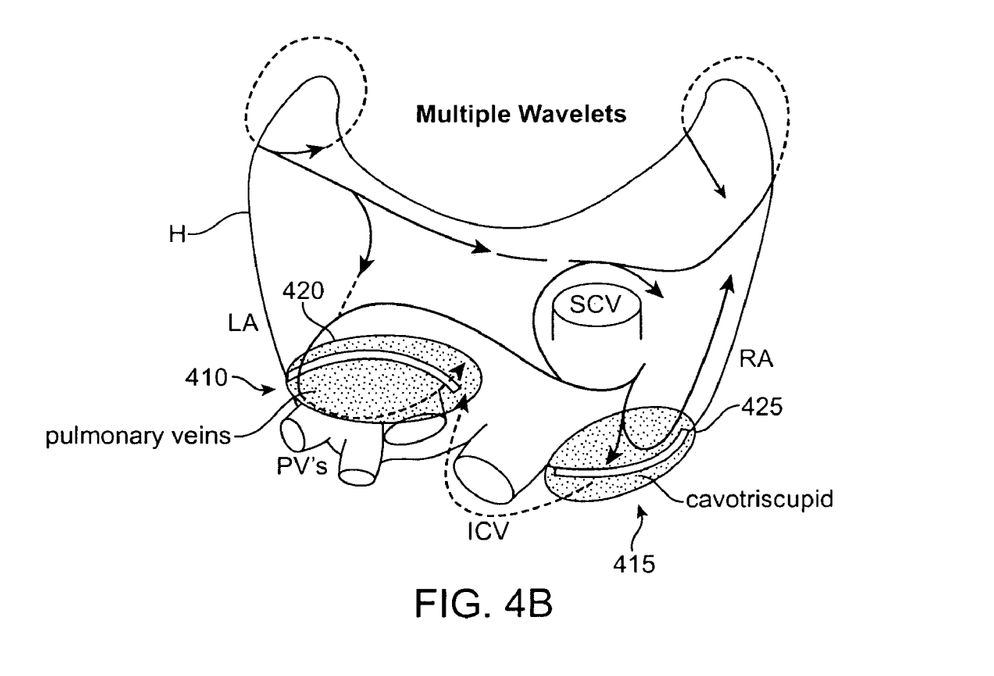

As pointed out above, system 10 is used for non-invasive radiosurgical ablation of the myocardium at one or more anatomical sites of a beating heart H of a patient. FIGS. 4A and 4B illustrate two possible sites, the left superior pulmonary vein-left atrial junction 410 and the cavotricuspid isthmus (CTI) 415. The system creates a target shape 420 for the treatment of the left superior pulmonary vein-left atrial junction and a target shape 425 for the treatment for treatment of the cavotricuspid isthmus 415.

The target shape 420, 425 is a three-dimensional shape created to include portions of the myocardium to be ablated. The registration of the anatomical site is accomplished by combining or fusing two or more images from imaging equipment, such as a Computer Tomography (CT) scan, a Magnetic Resonance Image (MRI) scan, a sonogram, an X-ray, an angiogram, electrophysiologic map or PET scan. In one embodiment, at least two X-ray images are acquired using different X-ray photon energies to create the target shape. When creating the target shape, one or more fiducials may be used.

The system 10 creates the target shape to encompass (including or surrounding) the anatomical site. The anatomical site may include an ostium of a pulmonary vein (PV), a cavotricuspid isthmus (CTI), an Atrioventricular (AV) node or junction, Sinoatrial (SA) node, His-Purkinje fibers, or ablation of areas necessary to control and treat aberrant arrhythmias, an atrial or ventricular site, neural fibers near or adjacent to the heart (ganglionic) or neural fibers in the chest or neck.

The system also includes a particle beam radiation or x-ray radiation device that is capable of directing one or more doses of radiation from outside of the patient's body toward the target shape to ablate the target shape. The quantity of absorbed in a tissue is the "dose" with the SI unit Gray ($Gy=J/kg$). The dose is strongly dependent on the type of radiation and the time span, also called "dwell time". An application dose rate is the dose of radiation per time (delivered or received). The dose rate delivered by a source depends on the activity of the source and the radionuclide that it contains. Biological effects of the absorbed radiation are dependent on the type of radiation and the type of tissue which is irradiated. Both total radiation dose and dose rate are important, since damage caused by radiation can be repaired between fractionated doses or during low dose rate exposure. The target dose rate may be between 15 to 80 Gy, preferably, between 25 to 40 Gy to achieve histological change at the target site without harm to other tissue. In one embodiment, the accuracy of is better than 2 mm, which is within the range of cardiac motion certain portions of the heart at or within 2 mm plus or minus.

In some embodiments, the system disregards a portion of cardiac motion of the heart while creating the target shape or directing the particle beam or both. In one embodiment, disregarding the cardiac motion may include not compensating for small cardiac motion, for example, disregarding cardiac motion less than 2 mm. In another embodiment, disregarding cardiac motion may include disregarding cardiac motion in the direction where the motion is least. In other embodiments, disregarding cardiac motion includes disregarding cardiac motion in at least one orientation of cardiac motion, two orientations, or disregarding motion in three dimensional space. In other embodiments, the target shape also includes compensating for respiratory motion, or the combination of respiratory motion and cardiac motion greater than 2 mm. Respiratory motion may be done in many different ways, for example, the motion may be monitored using a vest with LEDs worn on the patient's chest. Other motion may be detected using x-ray imagine. In other embodiments, the target shape includes only compensating for motion greater than 2 mm.

Figure 5:
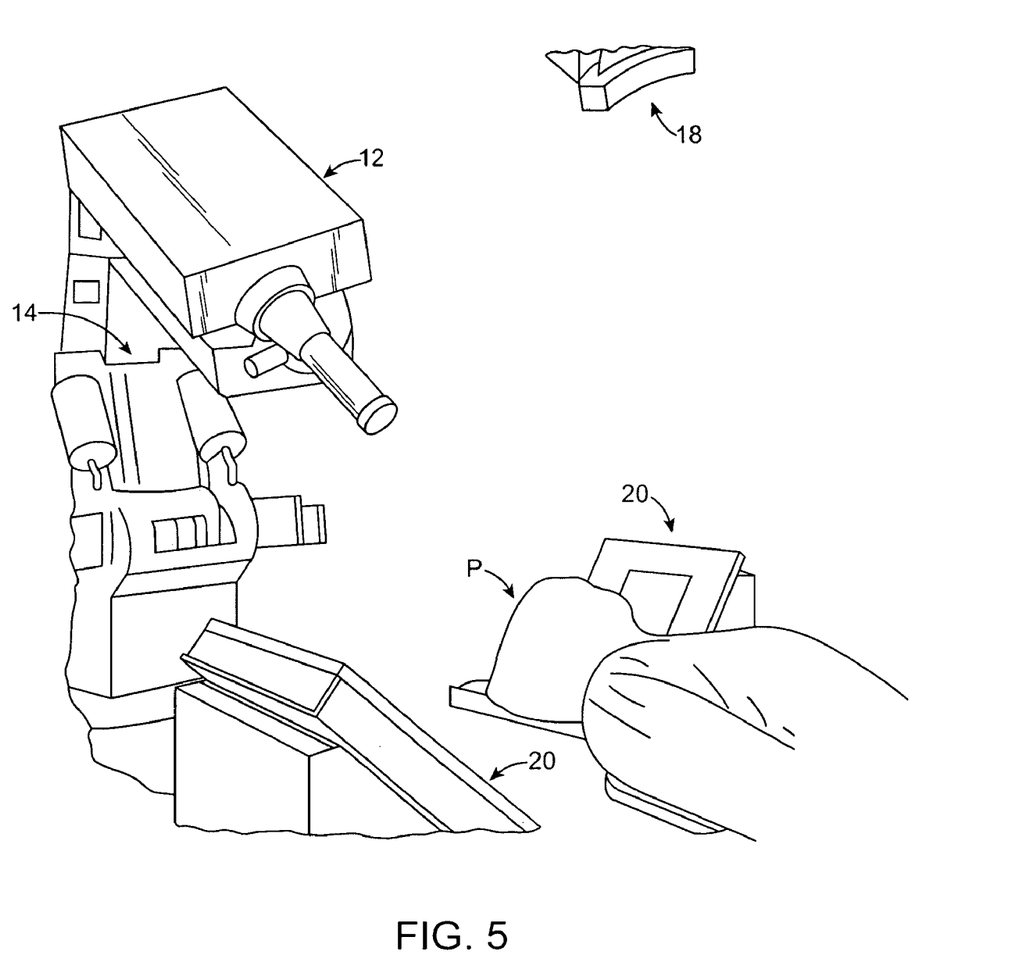
FIG. 5 illustrates stereotactic radiosurgery using the system of FIG. 1.
Figure 6:
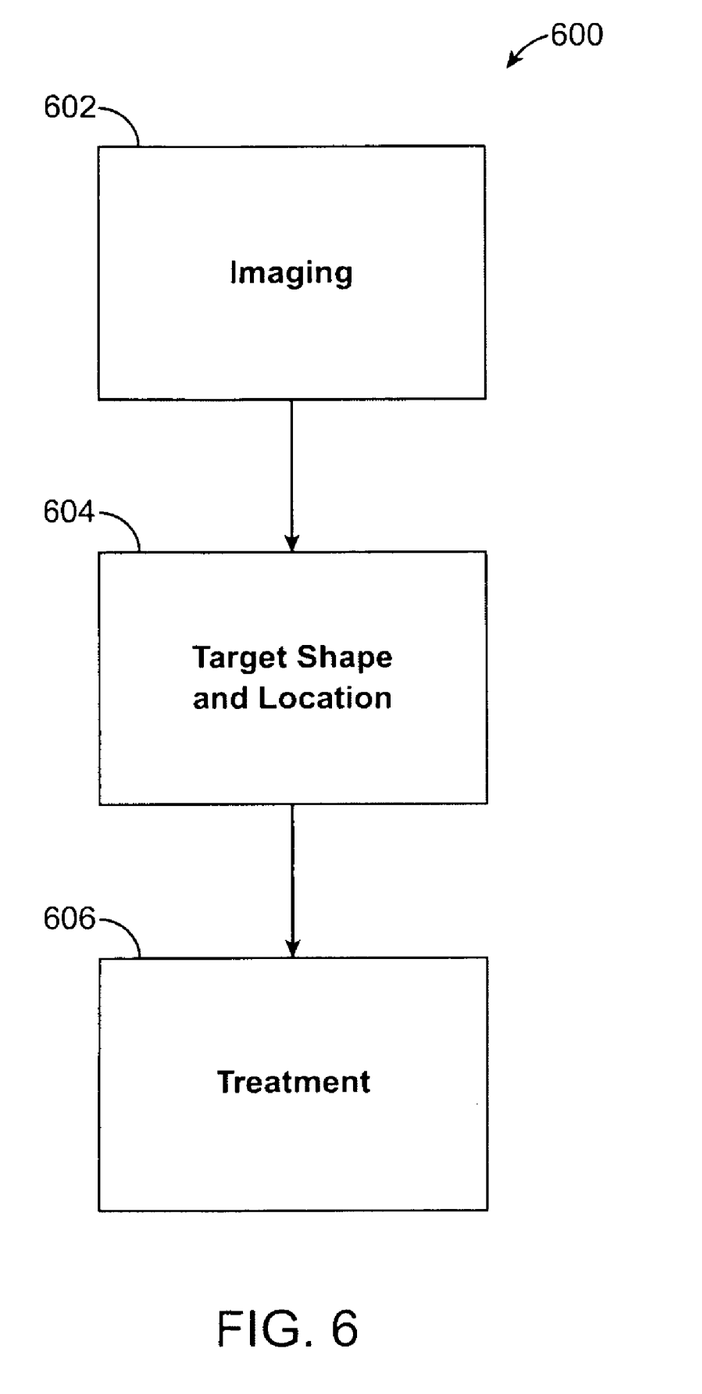
FIG. 6 is a flowchart schematically illustrating a radiosurgery treatment method.

A method for treating a target tissue can be understood with reference to FIGS. 5 and 6. Method 600 for using system 10 consists of imaging scans 602, creating a target shape 604 and treatment 606.

The imaging scans 602 or procedures are done by scanning the patient using one or more imaging devices, such as a Computer Tomography (CT) scan, a Magnetic Resonance Image (MRI) scan, a sonogram, an X-ray, an angiogram or an electrophysiologic map, which are then digitally transferred to the system 10. Two or more imaging scans are used to create the target shape and location 604 encompassing the anatomical site. The system disregards at least one orientation of cardiac motion, as discussed above. A patient considered for system by treatment 10 may be assessed extensively by a team comprised of a treating neurosurgeon, radiation oncologist, electrophysiologist, cardiologist, and/or physicist to determine whether radiation is appropriate and how much. As discussed above, one or more fiducials may by used, in conjunction with high quality imaging scan, provide three-dimensional stereotactic localization.

On the imaging scans 602, the surgeon and radiation oncologist identify the exact size, shape and location of the target and the surrounding vital structures to be avoided. Once the anatomy has been defined, the system software combines two or more of the images to create the target shape 604. Once the target shape 604 is complete, the system determines the number, intensity, and direction of radiation beams the robot will crossfire in order to insure that a sufficient dose is administered to the target shape without exceeding the tolerance of the adjacent tissue. The beams are fired from multiple angles 606. While some of the radiation may hit surrounding tissues, there is a relatively steep dose gradient. System 10 is capable of treating regions larger than 3-4 cms in diameter.

Sophisticated software allows for complex radiation dose planning in which critical structures are identified and protected from harmful levels of radiation dose. System 10 is capable of irradiating with millimeter accuracy. System 10 also has the ability to comprehensively treat multiple target shapes 604.

Advantages of the inventive approach over surgical intervention should be immediately apparent. Surgical approaches are necessarily invasive, and are associated with significant morbidity. The distinction applies to even more limited surgical procedures for electrical isolation of discreet atrial regions, including for example, atriotomy, RF ablation, and cryoablation. The inventive subject matter discussed herein provides ways to perform the ablation of ectopic pathways using focused, image-guided, completely non-invasive methods for energy delivery, effecting a complete treatment without the need for surgery or a percutaneous procedure. The procedure may be offered as an iterative treatment permitting minimal treatment, until the desired clinical result is attained. The procedure, being non-invasive, can be offered as an outpatient procedure without the associated need for an anesthetic or pain medication. Patients needing mitral valve repair concomitantly with atrial fibrillation therapy will likely be an early subset due to the potential of fiducial marker placement at the time of the valve intervention.

As illustrated in FIG. 5, during a procedure with system 10, a patient P lies still on a treatment table. Generally no sedation or anesthesia is used because the treatment is painless, and the procedure can last anywhere from between 30 to 90 minutes depending on the complexity of the case and the dose to be delivered. The treatment itself involves the administration of numerous radiation beams delivered from different directions, typically in 10 to 15 second bursts.

Advantageously, the novel treatments described herein can be iterative. Rather than target many foci or regions as is often done in an invasive procedure, externally applied radiosurgical ablation can address one or more target shapes on one day, and the then other target shapes on another day as needed. The interim period between treatments can be used to access the need for subsequent treatments. Such iterative or fractionated treatment is thus more conservative than current methods.

Suitable types of radiation, including particle beam radiation, may be employed. For example, the present invention encompasses the use of a GammaKnife™ radiosurgery system to ablate the myocardium. Although gamma radiation could be administered during open heart or other invasive procedures, the currently preferred applications are substantially non-surgical.

All suitable radiosurgery systems are contemplated with the energy source, duration and other parameters varying according to a size of the patient and other factors. A typical GammaKnife™ radiosurgery system may contain (for example) at least about 200 cobalt-60 sources of approximately 30 curies each, all of which are placed in an array under a heavily shielded unit. The shielded unit preferably comprises lead or other heavy metals.

Example 1

Cardiac Motion at Potential Sites for Non-invasive Ablation of Arrhythmias

Introduction: A non-invasive method for ablating cardiac tissue using externally focused radiation was done on an animal. This method compensates for motion associated with respiration by using a robotic arm to control the path of a high energy x-ray beam from a linear accelerator. Respiration is monitored by a vest with LEDs worn on the chest and other motion is detected by x-ray imaging in 2 planes. This method has been used successfully to treat lung tumors. However, it is not known to what extent targeting cardiac tissues for the treatment of arrhythmias may require compensation for cardiac contractile motion also.

Purpose: To determine the relative magnitudes of cardiac and respiratory movement at potential arrhythmia targets such as the left superior pulmonary vein (PV), AV junction (AVJ) and the cavo-tricuspid isthmus (CTI).

Method: Hanford-Sinclair mini-swine (40-70 kg) (n=5) were studied under anesthesia with either ventilation or spontaneous respiration. The femoral vein was cannulated and a CARTO mapping catheter (Webster-Biosense) was placed at the selected targets using fluoroscopy and electrograms to determine the precise the site. Measurement of the cardiac motion was done using CARTO with rapid sampling at each site for several respiratory cycles. Data was analyzed with custom software.

Results:

TABLE 1

Mean Maximal Motion at Cardiac Locations(Cardiac and Respiratory)(mm)

|  | X | Y | Z | X | Y | Z |
| --- | --- | --- | --- | --- | --- | --- |
| CTI | 1.08 | 1.14 | 0.86 | 1.90 | 5.14 | 1.60 |
| PV | 1.24 | 1.16 | 1.16 | 0.45 | 2.45 | 2.92 |
| AVJ | 2.42 | 3.19 | 2.57 | 1.07 | 3.73 | 0.95 |

A review of the results show motion related to cardiac contraction was much less than respiratory motion at the PV and CTI. At the AVJ, cardiac and respiratory motion were similar. Respiratory motion is usually largest in the vertical axis. At the PV and CTI cardiac motion is within the range of the accuracy of targeting (1-2 mm). The next step would be to acquire similar data in man to account for anatomic variations.

Conclusions: In swine, cardiac motion compensation is not needed at the PV and CTI but may be needed at other annular or ventricular sites. This motion compensation method could be useful for other robotic systems.

Example 2

Non-Invasive Ablation of the Left Superior Pulmonary Vein-Left Atrial Junction Using Stereotactic Focused Radiation Introduction: High energy x-ray irradiation from a linear accelerator mounted on a robot arm (Cyberknife) has been used to produce ablation of cardiac tissue in swine. This device is currently used in patients for diverse indications requiring careful targeting, from tumors to trigeminal neuralgia.

Conclusions: Selective targeting of cardiac arrhythmogenic sites can be done using stereotactically focused external radiation. The left superior pulmonary vein can be ablated without compensation for cardiac contractility.

Purpose: To determine if this method of energy delivery can be used to target potential arrhythmogenic sites such as the Left superior pulmonary vein-left atrial junction.

Method: Hanford-Sinclair mini-swine (40-70 kg) (n=9) were studied under anesthesia. The animals underwent radiation (x-rays, 40-80 Gray) using a computer controlled robotic arm (Cyberknife) which focused the x-ray beam on a preselected target. Targeting was done using either surgically implanted fiducials or fully non-invasively using a CT scan. A proprietary system was used to radiate the target while minimizing the dose to surrounding structures. Motion compensation was made for respiration during radiation, but no cardiac contractile motion compensation was made. The animals were then studied 4-8 weeks later with construction of cardiac voltage maps using CARTO (Webster-Biosense). Following this the animals were sacrificed and specimens taken for pathology.

Results: All animals survived treatment. Radiation to the left superior pulmonary vein eliminated local electrograms with voltage less than 0.1 mv.

Limitations: This study was done in swine and human pulmonary vein response to this treatment is unknown. This model was arrhythmia free and the efficacy of this treatment for atrial fibrillation is unknown.

While the exemplary embodiments have been described in some detail, by way of example and for clarity of understanding, those of skill in the art will recognize that a variety of modification, adaptations, and changes may be employed. For example, multiple energy sources may be employed, including laser or other photoenergy sources, in combination with one or more forms of radiation. Hence, the scope of the present invention may be limited solely by the appending claims.

What is claimed is:

1. A method for treatment of an anatomical site related to arrhythmogenesis of a heart of a patient, the method comprising:
   creating a target shape encompassing the anatomical site;
   directing particle beam radiation or x-ray radiation from outside the patient toward the target shape during a procedure, wherein one or more doses of radiation ablates the target shape;
   repeatedly obtaining images of the patient;
   identifying movement of the target in response to the images, the identified movement of the target comprising cardiac motion and respiratory motion;
   adjusting a location of the particle beam radiation or x-ray radiation during the procedure so as to compensate for the respiratory motion; and
   disregarding at least one orientation of the cardiac motion while creating the target shape or directing the particle beam or both.

2. The method of claim 1, wherein disregarding the cardiac motion includes not compensating for cardiac motion of less than 2 mm.

3. The method of claim 1, wherein disregarding the cardiac motion includes disregarding cardiac motion in the direction along which the motion is the least.

4. The method of claim 1, wherein disregarding the cardiac motion includes disregarding cardiac motion in two orientations.

5. The method of claim 1, wherein disregarding the cardiac motion includes disregarding motion along three orientations in three dimensional space.

6. The method of claim 1, wherein directing the particle beam radiation or x-ray radiation from outside the patient toward the target shape is done with an accuracy tighter than 2 mm.

7. The method of claim 6, wherein a range of the cardiac motion within the target is less than 2 mm.

8. The method of claim 1, wherein the anatomical site includes an ostium of a pulmonary vein (PV).

9. The method of claim 1, wherein the anatomical site includes a cavotricuspid isthmus (CTI).

10. The method of claim 1, wherein the patient has ventricular tachycardia and/or ventricular fibrillation and the anatomical site includes a valve annulus, a ventricular site, ventricular outflow tract, or a ventricular aneurysm.

11. The method of claim 1, wherein compensating for the respiratory motion includes compensating for motion greater than 2 mm.

12. The method of claim 11, wherein the anatomical site includes a pulmonary vein (PV).

13. The method of claim 11, wherein the anatomical site includes a cavotricuspid isthmus (CTI).

14. The method of claim 11, wherein the anatomical site includes an Atrioventricular (AV) node or junction, Sinoatrial (SA) node, or His-Purkinje fibers.

15. The method of claim 11, wherein the anatomical site includes an atrial or ventricular site.

16. The method of claim 1, wherein the anatomical site includes neural fibers near or adjacent to the heart (ganglionic) or neural fibers in the chest or neck.

17. The method of claim 1, wherein creating the target shape includes combining two or more images selected from the group consisting of a Computer Tomography (CT) scan, a Magnetic Resonance Image (MRI) scan, a sonogram, an X-ray, an angiogram, electrophysiologic map or PET scan.

18. The method of claim 1, wherein creating the target shape includes using one or more fiducials.

19. The method of claim 1, wherein the one or more doses is between 15-80 Gy.

20. The method of claim 1, wherein creating a target shape includes determining anatomical structures proximate to the target shape when determining a dose strength of the one or more doses.

21. A system for treatment an anatomical site related to arrhythmogenesis of a heart of a patient, the system comprising:
   an apparatus configured to create a target shape encompassing the anatomical site, wherein the apparatus disregards at least one orientation of cardiac motion, including not compensating for cardiac motion of less than 2 mm;
   a particle beam radiation or x-ray radiation device configured to direct one or more doses of radiation from outside the patient toward the target shape to ablate the target shape; and
   an image guidance system coupled to the particle beam radiation or x-ray radiation device, the image guidance system including:
      an image capture device configured to obtain a series of images of the patient, and a processor configured to determine changes in position of the target tissue using the series of images, the changes in position comprising the cardiac motion and respiratory motion wherein the system is configured to adjust a location of the particle beam or x-ray radiation in response to the series of images so as to track the respiratory motion of the target.

22. The system of claim 21, wherein the apparatus is configured to disregard at least one orientation of the cardiac motion by disregarding cardiac motion in the direction along which the motion is the least.

23. The system of claim 21, wherein the apparatus is configured to disregard at least one orientation of the cardiac motion by disregarding cardiac motion in two orientations.

24. The system of claim 21, wherein the apparatus is configured to disregard at least one orientation of the cardiac motion by disregarding the cardiac motion in three orientations of three dimensional space.

25. The system of claim 21, wherein the apparatus is configured to create the target shape by combining two or more images selected from the group consisting of a Computer Tomography (CT) scan, a Magnetic Resonance Image (MRI) scan, a sonogram, an X-ray, an angiogram, electrophysiologic map or PET scan.

26. The system of claim 21, wherein the apparatus is configured to create a target shape using one or more fiducials.

27. The method of claim 1, wherein disregarding the cardiac motion includes not compensating for cardiac motion of less than 2 mm and compensating for cardiac motion of greater than 2 mm.

28. The method of claim 1, wherein disregarding the cardiac motion includes disregarding cardiac motion only in the direction along which the motion is the least.

29. The method of claim 1, wherein disregarding the cardiac motion includes disregarding cardiac motion only in two orientations.

30. The method of claim 1, wherein disregarding the cardiac motion includes disregarding motion in all three dimensions.

31. A method for treatment of an anatomical site related to an arrhythmia of a heart of a patient, pumping of the heart inducing cardiac motion of the anatomical site in three dimensional space, the three-dimensional space defined by three orientations, the method comprising:

creating a target shape encompassing the anatomical site;

directing particle beam radiation or x-ray radiation from outside the patient toward the target shape during a procedure, wherein one or more doses of radiation ablates the target shape;

repeatedly obtaining images of the patient;

identifying movement of the target in response to the images, the identified movement of the target comprising cardiac motion and respiratory motion;

adjusting a location of the particle beam radiation or x-ray radiation during the procedure so as to compensate for the respiratory motion; and disregarding at least one of the orientations of the cardiac motion while creating the target shape or directing the particle beam or both, wherein the directing of the particle beam radiation or x-ray radiation mitigates the arrhythmia.

32. A system for treatment an anatomical site related to an arrhythmia of a heart of a patient, pumping of the heart inducing cardiac motion of the anatomical site in three dimensional space, the three-dimensional space defined by three orientations, the system comprising:

an apparatus configured to create a target shape encompassing the anatomical site; and a particle beam radiation or x-ray radiation device configured to direct one or more doses of radiation from outside the patient toward the target shape during a procedure to ablate the target shape such that the arrhythmia is mitigated;

an image guidance system coupled to the particle beam radiation or x-ray radiation device, the image guidance system including:

an image capture device configured to obtain a series of images of the patient, and a processor configured to determine changes in position of the target tissue using the series of images, the changes in position comprising the cardiac motion and respiratory motion;

wherein the apparatus is configured to disregard at least one of the orientations of the cardiac motion, including not compensating for cardiac motion of less than 2 mm along the at least one orientation when creating the target shape or directing the radiation or both, and to adjust a location of the particle beam or x-ray radiation in response to the series of images so as to track the respiratory motion of the target.

* * * * *